United States Patent
Wim

(10) Patent No.: US 6,187,021 B1
(45) Date of Patent: Feb. 13, 2001

(54) EAR CLEANING PORTABLE ROTARY DEVICE

(76) Inventor: Becker Wim, 2626 Silverfalls Dr., Kingwood, TX (US) 77339

( * ) Notice: Under 35 U.S.C. 154(b), the term of this patent shall be extended for 0 days.

(21) Appl. No.: 09/471,437

(22) Filed: Dec. 23, 1999

(51) Int. Cl.[7] .................................................. A61F 9/00
(52) U.S. Cl. .......................................... 606/162; 606/161
(58) Field of Search .................................. 606/162, 161; 604/1–5, 22; D24/249; D4/118, 135

(56) References Cited

U.S. PATENT DOCUMENTS

| 5,209,757 | 5/1993 | Krug et al. |
| 5,374,276 | 12/1994 | Lay. |
| 5,496,338 * | 3/1996 | Miyagi et al. ........................ 606/162 |
| 5,632,756 | 5/1997 | Kruglick. |
| 5,888,199 | 3/1999 | Karell et al.. |
| 5,931,845 * | 8/1999 | Amyette ............................... 606/162 |

* cited by examiner

*Primary Examiner*—Michael Buiz
*Assistant Examiner*—Lien Ngo
(74) *Attorney, Agent, or Firm*—Wendy K. Buskop; Buskop Law Group

(57) ABSTRACT

A portable electric motor driven ear cleaning device consisting of a rotary brush having soft hairs, a body, having a brush holder, which is capable of receiving and engaging the rotary brush and wherein the body is of three portions, a shoulder portion, a central body and an end and wherein the shoulder portion is tapered so that when the brush is inserted in the ear canal, the shoulder portion prevents ear drum penetration by said brush.

18 Claims, 5 Drawing Sheets

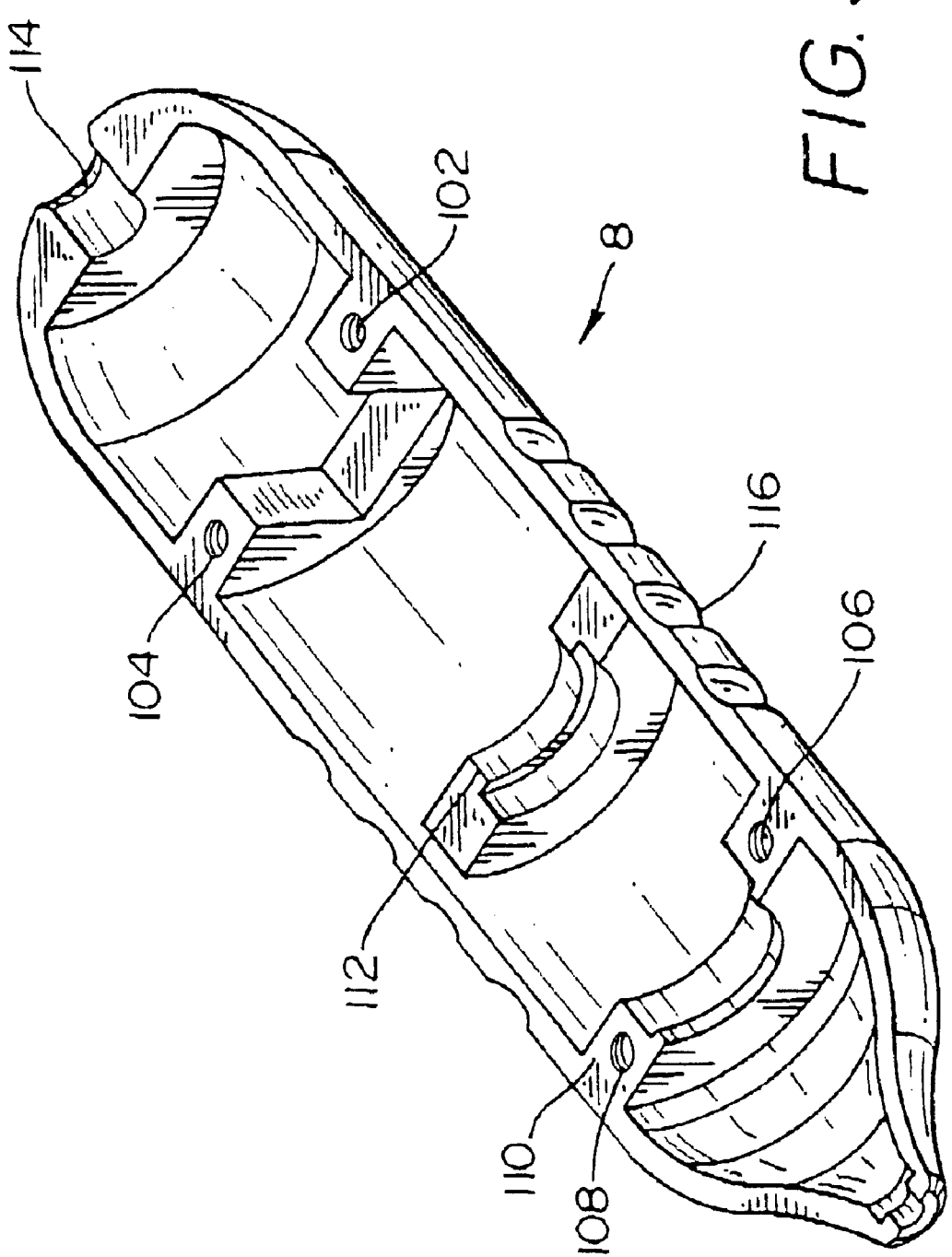

EAR CLEANING PORTABLE ROTARY DEVICE

BACKGROUND OF INVENTION

1. Field of Invention

The instant invention relates generally to human and animal body tubular passage cleaning devices and more specifically it relates to a portable ear-cleaning device.

2. Description of Prior Art

Wax build up in an ear canal prevents hinders hearing and reduces the ability to provide an adequate examination of the eardrum. Conventionally, earwax has been removed with a cotton swab, which tends to act as a plunger causes impaction or injury to the eardrum. Alternatively, doctors in the specialty frequently use water squeezed into the ear to loosen the wax and thereby assist in the removal of the offending material. To help prevent injury earwax cleaners (ear curette) were provided with depth control as in U.S. Pat. Nos. 5,334,212 and 5,509,921 to Karell, 1994 and 1996. U.S. Pat. No. 5,374,276 to Lay, 1994 and U.S. Pat. No. 5,632,756 to Kruglick, 1997, show ear cleaners combined with a swab.

Typical ear cleaning devices include those described in U.S. Pat. No. 5,632,756 a bulbous device or in U.S. Pat. No. 5,209,757, which describes an illuminated ear-cleaning device. Additionally, a conventional ear-cleaning device having a flexible part is described in U.S. Pat. No. 5888199. None of these devices teach a rotary ear-cleaning device using soft hairs, which hang limp when not in use and extend outwardly when in use. The present invention utilizes the soft hair concept, much like the novel car wash brushes, solving different problems then these conventional ear cleaners.

SUMMARY OF THE INVENTION

An important goal of an ear cleaner is to prevent eardrum injury while providing ease of use for laypersons and professionals. What is needed and is presented in the instant invention is a means for making the device safer while increasing the ability to remove the wax.

A primary object of the present invention is to provide an ear-cleaning device that will overcome the shortcomings of the prior art devices. Prior devices required a doctor's visit for irrigation of an ear canal. Prior devices were not depth sensitive, and penetration of and eardrum could occur. Prior devices did not have removable, disposable brushes engagable with a portable device, and caused additional ear infections.

Normal ear swabs have limitations in that bits of cotton could be left in the ear canal. Alternatively, as a swab is inserted in the ear, bits of dead skin cells could be pushed up against the ear drum and cause hearing problems or puncture an eardrum.

An object of the present invention is to overcome these problems and provide a device, which a normal lay person can use, which is depth controlled, and has disposable hair on the brush and is capable of cleaning out earwax safely and hygienically.

Further objects of the invention will appear as the description proceeds. To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF DRAWINGS

FIG. 5 shows a cross section view of a preferred embodiment of the body of the ear-cleaning device

DETAILED DESCRIPTION OF THE PRESENT INVENTION

Figure 1:
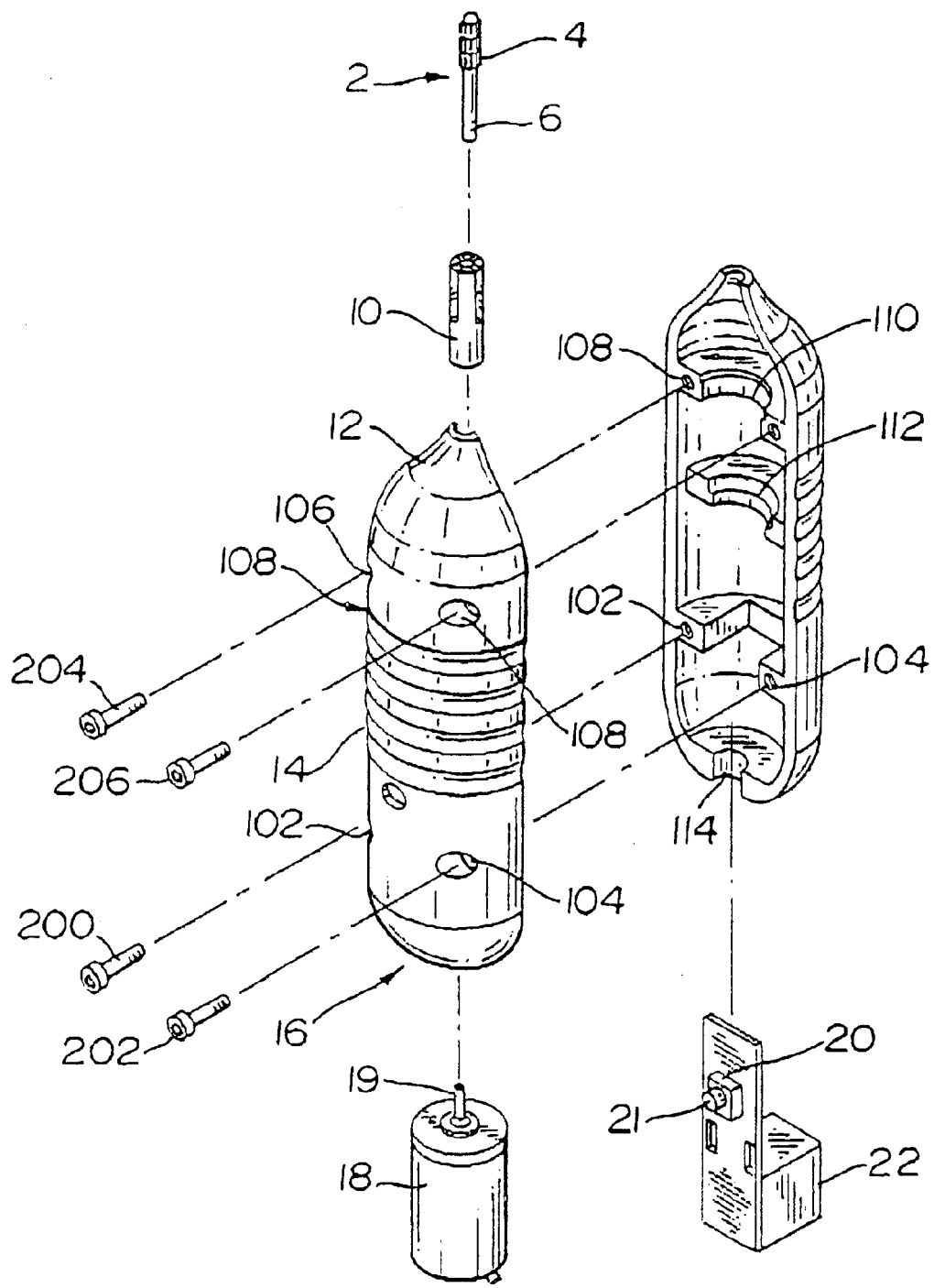
FIG. 1 is a perspective view showing a preferred embodiment of the present invention.

In FIG. 1, the instant invention comprises a brush (2) which is constructed of a brush element (4) and a rod (6).

Figure 2:
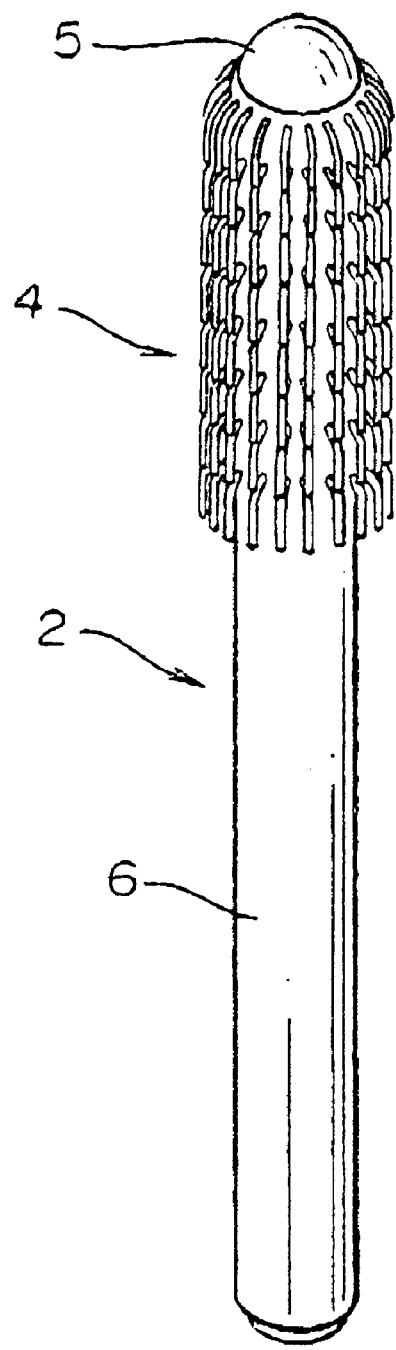
FIG. 2 is a perspective view of the brush.

Further details of the brush are shown in FIG. 2. In the preferred embodiment, the brush is made up of hairs (5). Any number of hairs can be used, depending on the brush size desired, although between 1 to over 5000 hairs are contemplated as usable in the preferred embodiment. In a preferred embodiment, between 1 and 2000 hairs are considered usable in the invention. In the most preferred embodiment, 1600 hairs are used on the brush.

The thickness and amount of hairs used will depend on the material chosen as the hairs on the brush. It is contemplated that the hairs can be made from a variety of materials, such as but not limited to, polymeric hairs made from polyethylene, polypropylene or mixtures of polyethylene and polypropylene, or any of the normal alpha olefins, soft horse hair, hairs made from elastomeric material, hairs made from blends of rubber and synthetic, coated hairs, or other types of materials, such as cotton or cellulose fibers. Nylon hairs are considered the material of the preferred embodiment, such as nylon 6,6. It may even be possible to use human hair if a sufficient quantity of hairs is used. Coated fibers and mixtures of any of the above materials are considered as usable as hairs within the scope of the present invention.

The key feature of the invention is that the brush portion of the portable rotary ear cleaner uses numerous hairs, which are limp, when the brush is not rotating. By "limp", it is meant that the hairs are not extended, that they are hanging downwardly, and are affected by gravity. These hairs must be able to extend outward when the brush is rotated enabling the otherwise limp hair to spin as the brush spins, with gravity causing the hairs to extend outwardly, by centrifugal force. In this way, the extended soft hairs touch the ear canal, engaging the earwax. Preferably at least one or more of the hairs captures a portion of the wax or dirt lying in the ear canal thereby cleaning the ear.

It is considered preferred that the hairs then be able to sustain washing, such as with soap or water to remove the wax, which is engaged with the brush.

It is an important feature of the present invention to use these soft hairs, and not to use rigid hairs, which could damage an ear canal or cause redness or abrasion. Rigid hairs, which could not work, would be rigid pointed plastic hairs, such as on a hairbrush. It is the softness of the hair, which is critical to the invention, as they prevent damage, which may occur to the ear canal when using a rigid element. The preferred embodiment of the present invention would use soft hairs having a length of between 0.5 and 1.5 mm and preferably 0.7 mm in length.

The brush element portion, which contains the hairs, can be of a variety of lengths depending on the type of animal or human the ear-cleaning device is intended. In a preferred embodiment, the brush element has an overall length, which is substantially equivalent to the ear canal being cleaned. Different lengths and diameters are considered within the scope of the present invention. It is contemplated that the brush overall length is between 1 and 20 mm. For example a small diameter and short length brush element would be appropriate as a child's ear cleaning brush. Such a brush might be between 2 and 3 mm in length. Similarly, the child's diameter might be 0.5 mm in diameter. In contrast, a teenager might require a brush portion having a medium diameter and medium length, such as 5 mm length and a 0.75 diameter. Along those same lines, an adult size brush portion might be a long as 10 mm in length and a diameter of up to 2.0 mm. Of course, when the brush portion is rotated, the diameter of the rotating brush with the hairs extended would be up to 3 mm for an adult. Similar dimensions would apply to the rotating brush for teenagers and children.

For animals, this invention could have different brush lengths than those stated for humans; the size of the animal's brush would depend on the actual ear canal depth of that animal. The "cat" version might be very short and about the size of an infant's brush. For dogs, there might be 3 sizes of brushes depending on the size of the dog. It is even possible that this device could be used on zoo animal's ears, such as Rhino's, goats, or sheep or possibly on monkeys or on gorillas.

In the preferred embodiment, it is contemplated that for an adult human, the length of the brush element would be up to 10 mm but could range between 0.5 mm to over 20 mm depending on how large the man is. Basketball players might need very large brushes, as they are very large men.

It is contemplated that the brush element can be rotated in either a clockwise or a counterclockwise direction by the motor contained within the body of the invention. Alternatively, it is contemplated that the brush can be used with an oscillating motion, moving in less than 360 degrees in order to remove the wax from the ear, in a "back and forth" non-circular motion and still accomplish the same ear cleaning objective. In the most preferred embodiment, the brush can be used either vertical to the plane of the ear canal or horizontal to the plane of the ear canal, in either a continuous motion or a pulsed motion to remove wax in the ear.

It is considered within the scope of this invention, that the term "foreign material" shall be defined as wax, or dirt particles or similar small particles lodged in the ear, including dead skin cells. It is also considered as within the scope of the invention that when wax is referred to herein, it also can be construed to apply to other foreign matter lodged in the ear canal.

Figure 3:
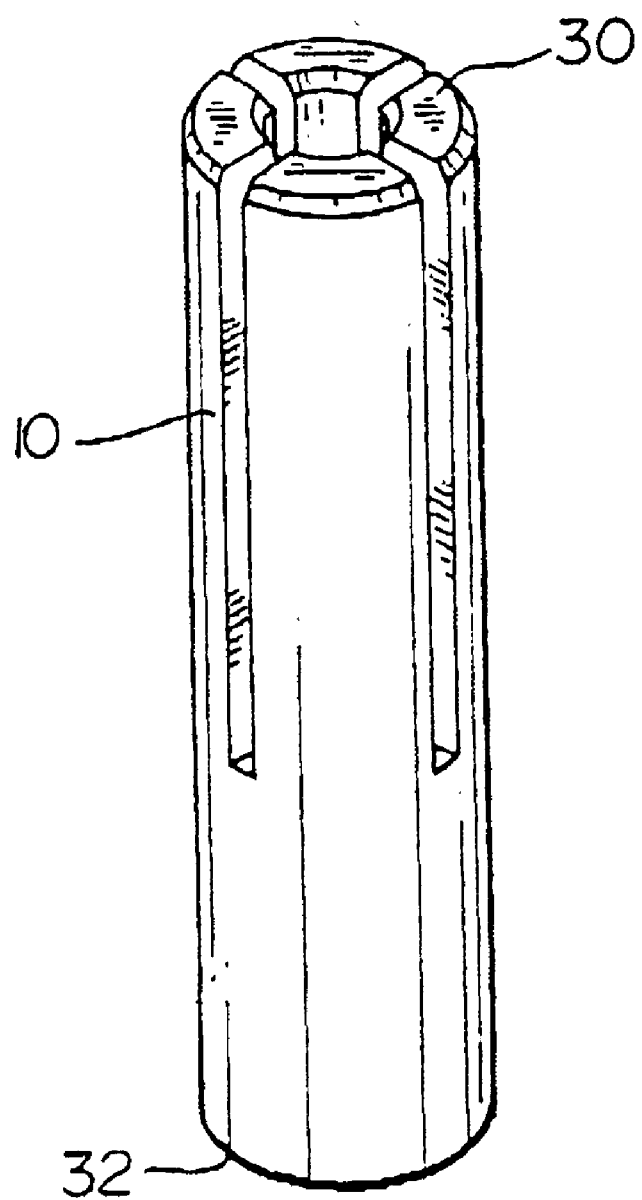
FIG. 3 is a perspective view of the brush holder of the present invention.

Referring again to FIG. 1, the rod (6) is inserted into a brush holder (10), which is disposed within the body (8) of the ear-cleaning device. A detail of the brush holder (10) is shown in FIG. 3. The brush holder (10) is capable of receiving and engaging said rod and providing a direct engagement with the motor extension (19) which enables rotation of the brush at the speed designated by the motor. Preferably, the brush holder has two sides as shown in FIG. 3, a first end for holding the brush (30) and a second end for connecting to the motor (32).

The motor is a DC (direct current) motor, which rotates the brush at RPM between about 1000 and 12,000 rpm. The most preferred rpm considered usable for an adult human ear would be approximately 8000 rpm for the brush. It is preferred that the motor be a micro motor to enable the device to be hand held and small. For example, a DC Minimotor FA model number 1219006G from Croglio, in Switzerland could be used in this invention. The motor (18) is disposed within said central body having a rotatably extension (19) on which a brush holder (10) is mounted. The motor is a DC electric motor capable of rotating said brush at a speed adequate to remove build up of wax in a human ear. Preferably the motor is a micro motor. These small motors are considered optimal because they are light, easy to use, and do not heat up during use. It is considered to be within the scope of the present invention to use any type of motor, such as a compressed air motor, or pump motor could be used. Any type of small mini motor that could generate up to 12,000 rpm could be used. It is contemplated to be within the scope of the present invention that the device can be a cordless device as well, such as one powered by solar energy or by batteries. It is important that the motor selected be very quiet so as not to disturb the hearing of the user during operation of the device.

The body (8) of the ear-cleaning device preferably comprises a shoulder portion (12), a central body (14) and an end (16). In the preferred embodiment, the body is substantially cylindrical, but other shapes for the body could be used as well. It is considered within the scope of the present invention that the body is square, triangular, rhombic or any other useful shape that can be held in the hand and used with ease.

The body is preferably made out of a rigid, non-corrosive material, such as stainless steel, or a spray painted metal, anything body which is capable of withstanding impact when dropped from a height of about 5 feet. The body is preferably compact and small, so that the device is not too heavy. The thickness of the body walls is about 2 mm, but other thicknesses could be used. The body in the preferred embodiment is of a two-part construction, which can be attached together in any conventional manner, such as by ultrasonic welding, or use of an adhesive or any attaching means, such as screws could be used.

Figure 4:
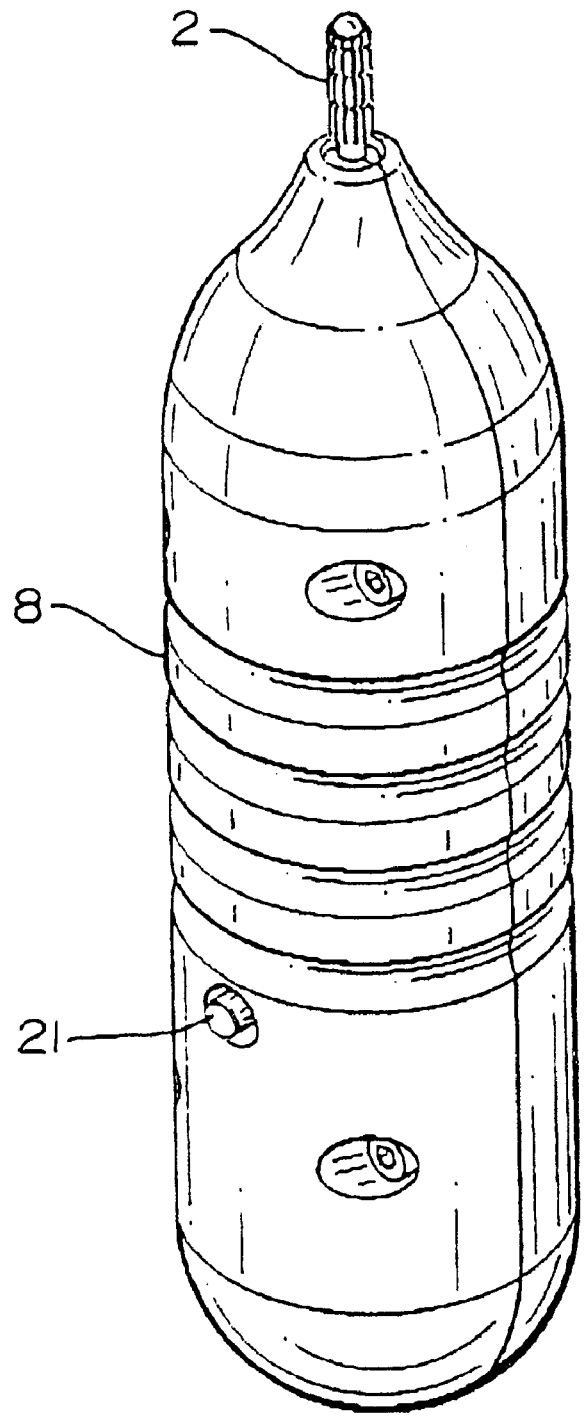
FIG. 4 is a perspective view of the assembled ear-cleaning device with the brush attached.

Alternatively, the body could be a one-part construction, created such as through blow molding, with the parts being inserted into the body through the end portion of the body. FIG. 4 shows a perspective view of the body of the ear-cleaning device with the brush attached.

FIG. 5 shows the embodiment of body of the ear-cleaning device, which involves two halves of the body, and means for holding the two halves together. More specifically, FIG. 5 shows a preferred embodiment of the present invention having attaching holes (102), (104), (106), and (108), into which screws shown in FIG. 1 as (200), (202), (204) and (206) respectively, can be inserted to hold the two halves of the body together. Ribs (110) and (112) are configured as part of the body and are used to keep the motor snugly in the interior portion of the body. A receptacle (114) for receiving the 110-volt current. The body (8) has optional gripping surfaces (116) disposed on a portion of the surface of the body (8) making the body easy to hold if a hand is wet.

At the end of the body 8, is receptacle 114 designed to receive 110 or 220 volt current directly into a transformer. The transformer (22) for transforming the current from AC to DC is directly connect to the motor (18). Any conventional transformer capable of handling from 3–12 volts could be used. In the preferred embodiment, a 6-volt transformer would be used. A usable transformer could be one available from Radio Shack, available anywhere in the United States.

It is preferred that the shoulder portion of the body be angled so that when the brush element (4) is inserted in the human ear, the shoulder portion prevents the brush from touching the eardrum. The shoulder portion is preferably angled at between 40–60 degrees, preferably at a 50 degrees angle. However, a shoulder angle of 1–180 could be used within the scope of the present invention.

A mini switch (20) is disposed within the body connected to said motor for turning on and off said motor and having actuation means (21) for turning on an off said motor. A typical switch usable herein would be a silicon rubber actuated surface mount switch would be one available from C N K components from Watertown, Mass.

It is contemplated that this device is a hand-held device, preferably weighing less than 1 kilo, preferably weighing 150–450 grams. Given the technology regarding micromotors and new lightweight composite materials that can be used on the body of this device, it is most preferred that this device is manufactured weighing only 250 grams. Regarding the weight issue, the device could be a wall mounted plug in unit, a "table top" or base mounted unit, or even a totally portable unit connected to a battery charger.

It is also contemplated that the device can be inserted into a holder for recharging if it is a battery or solar powered unit.

To operate the invention, the following steps should be taken:

Make sure the batteries are charged if a battery powered unit is used or make sure the power supply is plugged into the wall prior to initiating operation of the device.

Step 1: Grasp the body member (8) with the hand
Step 2: Insert the brush portion (2) into the brush holder (10) of the rotary ear-cleaning device
Step 3. Insert the brush portion 2 into the ear canal
Step 4. Make sure the brush portion 4 does not pierce the eardrum
Step 5: Engage the actuator 21 of the microswitch 20 to start rotation of the brush portion while in the ear canal
Step 6. Permit the brush portion to rotate approximately, 1–10 second to engage any particles of dirt in the ear or ear wax,
Step 7. Engage the actuator 21 to stop the rotation of the brush portion.
Step 8 Remove the brush portion from the ear canal
Step 9. Remove the brush portion (2) from the brush holder 10 by pulling the brush portion from the holder
Step 10. Cleaning the brush portion by running the brush portion under water, or soaking or any similar manner.

It will be understood that each of the element described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

What is claimed is:

1. A portable ear cleaning device comprising:
a brush comprising:
a brush element comprising a plurality of soft hairs which are limp when not rotating and which extend radially outward due to centrifugal force when rotating, and
a non-bending rod;
wherein the brush element has an overall length which is substantially equivalent to the length of the ear canal to be cleaned; and is between 1 and 20 mm in length
a body comprising:
a brush holder capable of receiving and engaging said rod at one end; and
further wherein said body comprises:
an tapered shoulder portion,
a central body, and
an end, and
further wherein said shoulder portion is tapered so that when the brush element is inserted in an ear canal, the shoulder portion prevents eardrum penetration by said brush element;
a motor disposed within said body having a rotatable extension protruding there from which can engage at one end, said brush holder;
a switch with actuation means disposed within said body connected to said motor for turning on and off said motor; and
a transformer for converting current from AC to DC current to engage said motor and rotate said brush.

2. The device of claim 1, wherein the brush element comprises soft hairs which are between about 0.5–1.5 mil in length.

3. The device of claim 2, wherein the soft hair length is 0.7 mm.

4. The device of claim 1, wherein the brush element comprises soft hairs made of a material which is selected from the group: nylon, polyethylene, polypropylene, elastomeric material, horse hair, human hair, coated fibers, cotton fibers, cellulose fibers, or mixtures thereof.

5. The device of claim 1; wherein the brush element is 7 mm in length.

6. The device of claim 1, wherein said body is substantially cylindrical and of a two-part construction.

7. The device of claim 1, wherein said motor is a DC electric motor capable of rotating said brush at a speed adequate to remove build up of foreign matter in an ear canal.

8. The device of claim 1, wherein said motor is a micro motor.

9. The device of claim 1, wherein the brush can be rotated in either a clockwise or a counterclockwise direction.

10. The device of claim 1, wherein the brush can move the soft hairs less than 360 degrees in order to remove the wax from the ear.

11. The device of claim 1, wherein the brush can be pulsed in a vertical motion relative to the plane of the ear canal in order to remove foreign matter from the ear.

12. The device of claim 1, wherein said motor is extremely quiet when in operation.

13. The device of claim 1, wherein between 1 and 5000 soft hairs are used on the brush element.

14. The device of claim 1, wherein 1 and 2000 soft hairs are used on the brush element.

15. The device of claim 1, wherein the brush can be pulsed in a horizontal motion relative to the plane of the ear canal in order to remove foreign matter from the ear.

16. The device of claim 7 wherein the foreign matter is earwax.

17. The device of claim 7, wherein the motor is capable of rotating said brush between about 1000 and 12,000 rpm.

18. A battery operated portable ear cleaning device comprising:

a brush element comprising a plurality of soft hairs which are limp when not rotating and which extend radially outward due to centrifugal force when rotating: and a non-bending rod;
  wherein the brush element has an overall length which is substantially equivalent to the length of the ear canal to be cleaned, and is between 1 and 20 mm in length;

a body comprising:
  a brush holder fixedly connected to a motor and capable of receiving and engaging said rod, at one end and further wherein said body comprises:
    an tapered shoulder portion, a central body, and an end, and
    further wherein said shoulder portion is tapered so that when the brush element is inserted in an ear canal, the shoulder portion prevents eardrum penetration by said brush element;
  a motor disposed within said body having a rotatable extension protruding there from which can engage at one end, said brush holder;
  a switch with actuation means disposed within said body connected to said motor for turning on and off said motor; and
  a transformer for converting current from AC to DC current to engage said motor and rotate said brush.

* * * * *

UNITED STATES PATENT AND TRADEMARK OFFICE
CERTIFICATE OF CORRECTION

PATENT NO. : 6,187,021 B1  
DATED : February 13, 2001  
INVENTOR(S) : Beckers

Page 1 of 1

It is certified that error appears in the above-identified patent and that said Letters Patent is hereby corrected as shown below:

<u>Title page,</u>
Item [76], please delete "Becker Wim", and insert the following therefore: -- Wim Beckers --.

Signed and Sealed this

Twenty-ninth Day of January, 2002

Attest:

Attesting Officer

JAMES E. ROGAN  
*Director of the United States Patent and Trademark Office*